United States Patent [19]

McIntosh

[11] Patent Number: 4,935,232
[45] Date of Patent: Jun. 19, 1990

[54] MICROBIOCIDAL COMPOSITION AND METHOD OF PREPARATION THEREOF

[75] Inventor: Robert H. McIntosh, Greensboro, N.C.

[73] Assignee: Interface Research Corporation, Atlanta, Ga.

[21] Appl. No.: 47,561

[22] Filed: Apr. 27, 1987

Related U.S. Application Data

[63] Continuation-in-part of Ser. No. 781,710, Oct. 2, 1985, abandoned, which is a continuation-in-part of Ser. No. 635,728, Jul. 7, 1984, abandoned, which is a continuation-in-part of Ser. No. 658,695, Oct. 9, 1984, abandoned, which is a continuation-in-part of Ser. No. 713,445, Apr. 18, 1985, abandoned, which is a continuation-in-part of Ser. No. 736,652, May 21, 1985, Pat. No. 4,647,601, which is a continuation-in-part of Ser. No. 744,916, Jun. 13, 1985, abandoned, which is a continuation-in-part of Ser. No. 744,730, Jun. 13, 1985, abandoned, which is a continuation-in-part of Ser. No. 570,952, Mar. 8, 1984, Pat. No. 4,608,289, which is a continuation of Ser. No. 523,734, Aug. 16, 1983, abandoned, which is a continuation of Ser. No. 226,006, Jan. 19, 1981, abandoned, which is a continuation of Ser. No. 930,879, Aug. 4, 1978, abandoned.

[51] Int. Cl.$^5$ ............................................. A61K 31/74
[52] U.S. Cl. ........................................ 424/78; 424/81; 424/82; 424/83; 424/400; 424/402; 424/404; 424/405; 424/409; 424/443
[58] Field of Search ................ 424/78, 81, 76.8, 82, 424/83, 443, 400, 402, 404, 405, 409; 252/106; 106/18.31; 514/76, 148, 143

[56] References Cited

U.S. PATENT DOCUMENTS

| | | | |
|---|---|---|---|
| 2,202,124 | 4/1940 | Tattersal | 106/18.17 |
| 2,237,424 | 4/1941 | Stoner et al. | 260/86 |
| 2,272,668 | 2/1942 | Honel | 558/113 |
| 2,541,088 | 2/1951 | Nikawitz | 260/584 |
| 2,552,325 | 5/1951 | Kosolapoff | 260/461 |
| 2,592,564 | 4/1952 | Hardman | 106/273 |
| 2,676,122 | 4/1954 | McCarthy | 117/139.5 |
| 2,756,175 | 7/1956 | Goldstein et al. | 167/33 |
| 2,831,782 | 4/1958 | Zvanut | 117/127 |
| 2,872,351 | 2/1959 | Wedell | 117/121 |
| 2,891,878 | 6/1959 | Chamberlain | 428/421 |
| 2,922,738 | 1/1960 | McDermott et al. | 167/22 |
| 2,935,490 | 5/1960 | Havens et al. | 260/45.7 |
| 2,960,529 | 11/1960 | McCall et al. | 260/461 |
| 2,970,081 | 1/1961 | McCall et al. | 167/30 |
| 2,976,186 | 3/1961 | Thompson et al. | 260/45.8 |
| 2,997,454 | 8/1961 | Leistner et al. | 260/45.8 |
| 3,247,134 | 4/1966 | Hwa et al. | 260/2.5 |
| 3,279,986 | 10/1966 | Hyman | 167/42 |
| 3,280,131 | 10/1966 | Wakeman et al. | 260/286 |
| 3,294,775 | 12/1966 | Wasserman | 260/100 |
| 3,294,775 | 12/1966 | Wasserman | 260/100 |
| 3,308,488 | 3/1967 | Schoonman | 5/355 |
| 3,312,623 | 4/1967 | Fitch et al. | 252/106 |
| 3,364,192 | 1/1968 | Leach | 260/94.9 |
| 3,404,140 | 10/1968 | Fukumoto et al. | 260/93.7 |
| 3,428,713 | 2/1969 | Bartlett et al. | 260/924 |
| 3,475,204 | 10/1969 | Patterson | 117/178.8 |
| 3,498,969 | 3/1970 | Lewis et al. | 260/211 |
| 3,527,726 | 9/1970 | Gower et al. | 260/29.6 |
| 3,577,515 | 5/1971 | Vandegaer | 424/32 |
| 3,620,453 | 11/1971 | Gancberg et al. | 239/60 |
| 3,639,594 | 2/1972 | Notarianni et al. | 514/76 |
| 3,641,226 | 2/1972 | Partridge et al. | 260/990 |
| 3,671,304 | 6/1972 | Mischutin | 117/138 |
| 3,705,235 | 12/1972 | McIntosh et al. | 424/83 |
| 3,708,573 | 1/1973 | Yoshinaga et al. | 260/29.6 |
| 3,714,256 | 1/1973 | Samour et al. | 260/29.6 |
| 3,758,283 | 9/1973 | Matt | 44/62 |
| 3,762,415 | 10/1973 | Morrison | 128/290 |
| 3,769,377 | 10/1973 | De Selms | 260/958 |
| 3,776,806 | 12/1973 | Mayer et al. | 161/88 |
| 3,793,408 | 6/1974 | Schulz | 260/990 |
| 3,819,656 | 6/1974 | Barie, Jr. et al. | 260/343.7 |

(List continued on next page.)

FOREIGN PATENT DOCUMENTS

1162356 2/1984 Canada.
0018492 11/1980 European Pat. Off.
0035375 9/1981 European Pat. Off.

(List continued on next page.)

OTHER PUBLICATIONS

Matsui et al., *Chem. Abstracts*, 82, 141561, (1974), (JP 74 24,806).

(List continued on next page.)

Primary Examiner—Thurman K. Page
Attorney, Agent, or Firm—Kilpatrick & Cody

[57] ABSTRACT

The present invention relates to microbiocidal compositions and methods for the preparation and use of of such compositions. Properly used in accordance with the present invention, these microbiocidal compositions are effective in killing or inhibiting a wide variety of harmful, destructive or offensive microorganisms including viruses, bacteria, yeasts, algae and molds. The microbiocidal compositions of the present invention are suitable for use with conventional detergents to provide microbiocidal cleansing agents. The microbiocidal compositions can also be mixed with a liquid to provide an effective disinfectant. The microbiocidal additive can be incorporated into plastic materials and various synthetic fibers thereby imparting microbiocidal activity to the plastic materials or fibers. In addition, the microbiocidal compositions of the present invention can be incorporated into a wide variety of permanent and nonpermanent coating materials including, but not limited to, paints, varnishes, epoxy coatings and waxes. The microbiocidal compositions can also be used as preservative for protecting wood and wood products from damage by microorganisms or insects. The microbiocidal compositions of the present invention can also be used to kill or repel insects.

15 Claims, No Drawings

U.S. PATENT DOCUMENTS

| | | | |
|---|---|---|---|
| 3,873,648 | 3/1975 | Balde | 260/990 |
| 3,885,000 | 5/1975 | Beriger et al. | 260/956 |
| 3,888,978 | 6/1975 | Duwel et al. | 424/199 |
| 3,896,101 | 7/1975 | McIntosh et al. | 260/93.7 |
| 3,897,491 | 7/1975 | Toy et al. | 523/122 X |
| 3,897,521 | 7/1975 | Beriger et al. | 260/948 |
| 3,919,410 | 11/1975 | McIntosh et al. | 424/78 |
| 3,920,836 | 11/1975 | McIntosh et al. | 424/315 |
| 3,925,442 | 12/1975 | Samour | 424/315 |
| 3,928,563 | 12/1975 | McIntosh et al. | 424/78 |
| 3,932,612 | 1/1976 | Burkhardt et al. | 424/78 |
| 3,933,947 | 1/1976 | Kishino et al. | 260/949 |
| 3,959,556 | 5/1976 | Morrison | 428/364 |
| 3,972,243 | 8/1976 | Driscoll et al. | 424/200 |
| 3,979,307 | 9/1976 | Kolaian et al. | 252/8.75 |
| 3,991,187 | 11/1976 | Hogberg et al. | 514/76 |
| 4,004,001 | 1/1977 | Large et al. | 424/200 |
| 4,006,204 | 2/1977 | Rajadhyaksha et al. | 260/958 |
| 4,024,324 | 5/1977 | Sparks | 526/2 |
| 4,025,583 | 5/1977 | Mead et al. | 260/925 |
| 4,039,636 | 8/1977 | Claus et al. | 260/963 |
| 4,071,552 | 1/1978 | Ferland et al. | 260/562 R |
| 4,083,860 | 4/1978 | Ruf | 260/403 |
| 4,094,970 | 6/1978 | Behrenz et al. | 424/78 |
| 4,107,292 | 8/1978 | Nemeth | 424/78 |
| 4,110,504 | 8/1978 | Hull et al. | 424/97 |
| 4,119,724 | 10/1978 | Thizy et al. | 424/45 |
| 4,139,616 | 2/1979 | Ducret et al. | 424/222 |
| 4,152,421 | 5/1979 | Tsutsumi et al. | 424/57 |
| 4,165,369 | 8/1979 | Watanabe et al. | 424/70 |
| 4,235,733 | 11/1980 | Watanabe et al. | 252/107 |
| 4,259,078 | 3/1981 | Kleber et al. | 8/188 |
| 4,272,395 | 6/1981 | Wright | 252/106 |
| 4,276,418 | 6/1981 | Howarth | 544/243 |
| 4,289,634 | 9/1981 | Lewis et al. | 252/32.5 |
| 4,343,853 | 8/1982 | Morrison | 428/233 |
| 4,361,611 | 11/1982 | Schafer et al. | 428/96 |
| 4,363,663 | 12/1982 | Hill | 523/122 X |
| 4,401,712 | 8/1983 | Morrison | 428/289 |
| 4,432,833 | 2/1984 | Breese | 162/138 |
| 4,442,095 | 4/1984 | Johnston | 544/120 |
| 4,442,096 | 4/1984 | Johnston | 424/250 |
| 4,560,599 | 12/1985 | Regen | 428/36 |
| 4,598,006 | 7/1986 | Sand | 424/81 |
| 4,647,601 | 3/1987 | McIntosh | 523/122 |
| 4,661,477 | 4/1987 | Gorog nee Privitzer | 514/76 |
| 4,770,694 | 9/1988 | Iwasaki et al. | 71/93 |

FOREIGN PATENT DOCUMENTS

| | | |
|---|---|---|
| 1228031 | 11/1966 | Fed. Rep. of Germany . |
| 2530584 | 1/1977 | Fed. Rep. of Germany . |
| 3014765 | 10/1981 | Fed. Rep. of Germany . |
| 3039437 | 5/1982 | Fed. Rep. of Germany . |
| 3248708 | 12/1982 | Fed. Rep. of Germany . |
| 2157952A | 7/1982 | Japan . |
| 617854 | 6/1980 | Switzerland . |
| 1122664 | 11/1984 | U.S.S.R. . |
| 1036578 | 7/1966 | United Kingdom . |
| 1302894 | 1/1973 | United Kingdom . |
| 2042574 | 9/1983 | United Kingdom . |
| 2131029 | 1/1986 | United Kingdom . |

OTHER PUBLICATIONS

Ogasawara et al., *Chem. Abstracts,* 81, 107078f, (1974), (U.S. Pat. No. 3,799,904).

Hall et al., *Chem. Abstracts,* 80, 123000, (1973), *ASLE Trans.,* 16(4), 291-296.

Keil et al., *Chem. Abstracts,* 76, 101944k, (1972), Ger. Offen. 2,030,256.

Sudakova et al., *Chem. Abstracts,* 70, 56711v, (1969), (USSR 229,879).

Gialkdi et al., *Chem. Abstracts,* 43, 6363a, (1949), (*Farm. sci. e tec.,* 4, 166-175).

Tak Chemicals Ltd., 1580026, (Jun. 1977).

McCoy, *Microbiology of Cooling Water,* 94-95, (Chemical Pub. Co., N.Y., 1980).

Yuan et al., *Phosphorus and Sulphur,* vol. 18, 323-326, (1983).

Nakamura, *Journal of Radioanalytical Chemistry,* 52 (2), 343-354, (1979).

Nakamura, *Journal of Radioanalytical Chemistry,* 44, 37-47, (1978).

Partridge et al., *J. Inorg. Nucl. Chem.,* 31, 2587-2589, (1969).

Tachimori et al., *Journal of Radioanalytical Chemistry,* 67 (2), 329-337, (1981).

Honaker et al., *J. Inorg. Nucl. Chem.,* 39, 1703-1704, (1977).

J. Perka et al., *Tenside Detergents,* 15, 295-298, (1978)6.

Sorbe et al., *Quim. Apl. Jorn. Com. Esp. Deterg.,* 11th, 415-430, (1980).

Yoshihira Koda et al., "The Synthesis of Surfactant and the Use Thereof", pp. 96-99 and 436-447, (1977).

Takehiko Fujimoto, "Introduction in New Surfactant", pp. 295-297, (1974).

*J. Inorg. Nucl. Chem.,* 38, 2127-2129, (1976).

MICROBIOCIDAL COMPOSITION AND METHOD OF PREPARATION THEREOF

CROSS-REFERENCE TO RELATED CASES

This is a continuation-in-part of application Ser. No. 781,710 filed on Oct. 2, 1985, now abandoned; 635,728 filed on July 7, 1984, now abandoned; application Ser. No. 658,695 filed on Oct. 9, 1984, now abandoned; application Ser. No. 713,445 filed on Mar. 18, 1985, now abandoned; application Ser. No. 736,652 filed on May 21, 1985 U.S. Pat. No. 4,647,607; application Ser. No. 744,916 filed on June 13, 1985 now abandoned; and application Ser. No. 744,730 filed on June 13, 1985, now abandoned; all of which are continuations-in-part of application Ser. No. 570,952 filed Mar. 8, 1984 Pat. No. 4,608,289, which in turn was a continuation of application Ser. No. 523,734 filed Aug. 16, 1983, now abandoned, which was a continuation of application Ser. No. 226,006 filed Jan. 19, 1981, now abandoned, which was a continuation of application Ser. No. 930,879 filed Aug. 4, 1978, also now abandoned.

TECHNICAL FIELD

The present invention relates to microbiocidal compositions and methods for the preparation and use of such compositions. Properly used in accordance with the present invention, these microbiocidal compositions are effective in killing or inhibiting a wide variety of harmful, destructive, or offensive microorganisms including viruses, bacteria, algae, yeasts, and molds.

BACKGROUND

Discussion of the present invention and its background will be facilitated by definition of several terms.

As used herein, the term "microorganism" means any organism that cannot easily be seen with the naked eye and includes organisms such as bacteria, molds, yeasts, fungi, algae and viruses. "Antimicrobial" and "microbiocidal" describe the killing of, as well as the inhibition of the growth of, bacteria, yeasts, fungi, algae, and molds. "Bactericidal" describes the killing or inhibition of the growth of bacteria. "Fungicidal" describes the killing of, as well as the inhibition of the growth of, fungi, yeasts and molds. The term "viricidal" is used to describe the inactivation of virus particles so that they are unable to infect host cells. The term "plastic," as used herein, includes both thermosetting and thermoplastic materials. Examples of "plastic" materials include, but are not limited to, polyolefins (such as polyethylenes, polypropylenes, polybutylenes) polystyrenes, vinyl phenolics, vinyl acetates, polymeric vinyl chlorides, ureas, melamines, acrylics, polyesters, epoxies, and nylons. The term "molded" as used in this application is used in its broad sense to include any technique for forming plastic or other materials. Molding is generally, but not always, accomplished with elevated temperature and includes, but is not limited to, forming methods such as potting, extruding, sheeting, calendering, pulltruding, casting, vacuum forming, blow molding, and the like.

The term "cleansing agent" includes any substance capable of cleaning, emulsifying, or removing unwanted material from a surface. The term "detergent" describes any substance or product which is capable of dislodging, removing, or dispersing solid and liquid soils from a surface being cleansed. The term "detergent" also includes soaps comprising metal salts of long chain fatty acids. The term "disinfectant" includes any liquid that is capable of killing or inhibiting microorganisms.

The term "free hydroxy" as used herein means an oxygen that is bonded to a phosphorus in a phosphate group.

Bacteria, fungi, viruses, algae and other microorganisms are always present in our environment. Such microorganisms are frequently an essential pat of ecological systems, industrial processes, and healthy human and animal bodily functions, such as digestion. In other intances, however, the presence of microorganisms is highly undesirable because they may cause illnesses or death of humans and animals, create odors and damage or destroy a wide variety of materials.

The species and numbers of microorganisms present vary depending on the general environment, on the nutrients and the moisture available for the growth of the microorganisms, and on humidity and temperature of the local environment. Nutrients for microorganisms abound in the normal environment. Any protein matter such as dried skin, discarded foods, plants, and animal wastes all are excellent nutrient media for many types of potentially harmful microorganisms. Furthermore, many organic synthetic and natural materials like plastic coatings and objects, and wood, paper and natural fibers can serve as nutrients for microorganisms which will degrade those materials. In addition, certain bacteria are capable of remaining viable in a dormant state on floors or on objects for long periods of time until they are deposited in the proper media for growth. Consequently, potentially harmful microorganisms can be transported merely by walking on floors, brushing against walls or furniture or by handling objects.

It is well recognized that a major difficulty in health care facilities, such as hospitals and nursing homes, is the spread of dangerous infectious diseases caused by a wide variety of microorganisms. The problem is exacerbated in these facilities because many of the patients are in a weakened condition due to their primary health care problem. A microorganism that would not be a major threat to a healthy person could be fatal to a patient with a diminished capacity to defend himself from infection.

Potentially dangerous microorganisms are spread in health care facilities and elsewhere by a variety of vectors. One of the most common vectors is health care personnel. For example, a nurse or doctor may administer care to one patient and then be called upon to treat a second patient. Even though he or she may carefully wash his or her hands before treating the second patient, potentially dangerous microorganisms may be transferred from the first patient to the second patient. The microorganism can then cause a serious infection in the second patient.

Furthermore, plastic products are often used in hospitals and other health care facilities. These products are particularly susceptible to contamination by bacteria and other harmful organisms. Conventionally, the plastic products in these facilities are periodically cleaned with strong cleansers to remove or kill accumulated microorganisms. Between these cleanings, however, it is possible for the plastic products to accumulate a sufficient quantity or quality of bacteria or other microorganisms to constitute a major vector for cross-infection or spread of infectious diseases.

Pathogenic microorganisms can also be deposited on fabrics such as towels, clothes, laboratory coats and other fabrics. These microorganisms can remain viable on these fabrics for long periods of time. If the fabrics are used by several different people, the microorganisms can be transferred by people walking from one part of the facility to another.

As mentioned above, the plastics that are used to make plastic objects and coatings can themselves be a substrate for growth of various microorganisms, such as bacteria, mold and mildew. The same is true for fibers and fabrics, some of which are plastics and other organic materials such as wood and paper. When these microorganisms grow on or in a plastic product, fiber, or fabric, they form unsightly colonies. In addition, such microorganisms can eventually break down a plastic, fiber, fabric, or other material. Plastic, fiber and fabric products often must therefore be frequently cleaned with a strong cleanser to destroy, or at least control, the growth of the microorganisms. A more effective approach to the problem is clearly needed.

Potentially destructive microorganisms also tend to collect and reside in clothing and in fabrics regardless of whether they provide a nutrient substrate. Clothing that is used when exercising is particularly susceptible to the accumulation of destructive microorganisms. If these microorganisms are not killed or inhibited, they may cause extensive damage to the fabric, not to mention causing offensive odors and infections. Washing with conventional detergents does not always kill or remove many of these microorganisms. Thus, a microbiocidal additive is needed that will kill or inhibit the microorganisms residing on the fabric and, at the same time, not cause deterioration of the fabric and not cause adverse physical reactions in the individual that is wearing the fabric.

In short, the control of microbial contamination and infection has been a major problem throughout history in both industry and the home, and such infection and contamination continues to cause disease, death, and destruction of property. It has proved difficult, however, to develop a microbiocidal additive that is effective in controlling the growth of a wide variety of unwanted microorganisms and is, at the same time, safe for use around human beings and animals. Accordingly, there is an acute need, both in industry and in the home, for a safe and effective microbiocidal additive that can be used in or on a wide variety of substances to impart microbiocidal activity to the product from which the substance is made.

One of the sources of difficulty in the control of potentially harmful microorganisms is the extreme variability of response of various microorganisms to conventional microbiocidal agents. For example, bacteria, which are classified as procaryotes, can be killed or inhibited by many different type of antibiotics. However, these same antibiotics that are effective against procaryotic organisms are usually ineffective against eucaryotic microorganisms, such as fungi and yeasts.

Even within the family of Bacteriaceae, there are two broad categories of bacteria known as Gram-positive and Gram-negative bacteria. These classifications stem from the ability or non-ability of bacteria to absorb certain vital stains, and the two groups of bacteria generally respond differently to the same microbiocidal agent. A particular agent that may be effective against one group may not be effective against the other group.

One conventional method of inhibiting the growth of both eucaryotes and procaryotes or both Gram-negative and Gram-positive bacteria is to combine two or more microbiocidal inhibitors, each designed to inhibit or kill a specific organism or class of organisms. However, various problems arise when introducing two or more additives into a material such as a detergent. The multiple additive system may alter the physical properties of the detergent into which it is mixed. In addition, the multiple components must be tested to insure compatibility and continued microbiocidal effectiveness when combined with the detergent. The relative microbiocidal or microbiostatic strength of each of the components in the multiple system must be determined. It is not uncommon for the combination of microbiocidal additives to initially have effective inhibiting or killing properties for both Gram-positive and Gram-negative organisms whereupon, with the passage of time, one or the other of the inhibiting additives will deteriorate and lose its effectiveness while the other inhibiting additive remains effective. In addition, one additive may have an unexpected inhibitory effect on the other additive. In addition, the requirement of adding two or more additives can become prohibitively expensive.

The ideal microbiocidal additive must be non-toxic to humans and animals around which the additive is used. Such an additive should not cause an allergic reaction and must have no long term detrimental health effects on humans or animals. Finally, such an microbiocidal additive should be compatible with the material with which is it being used and not cause the material to deteriorate or lose its desired properties.

SUMMARY OF THE INVENTION

The present invention solves the problem described above by providing a composition including a broad spectrum, safe, microbiocidal additive that is effective in killing or inhibiting a wide variety of microorganisms including viruses, bacteria, yeasts, molds and fungi and algae. The microbiocidal additive comprises a phosphate derivative having microbiocidal activity. The microbiocidal phosphate derivative has at least one free hydroxyl group thereon.

The microbiocidal additive of the present invention is a phosphate derivative with at least one free hydroxyl group. The phosphate derivative has the following general formula:

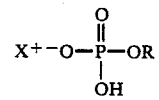

wherein:
R may be alkyl, aryl, aralkyl and alkaryl groups including, but not limited to, straight chain, branched chain or cyclic alkyl groups having from 1 to 24 carbon atoms, polyoxyethylene or polyoxypropylene having from 2 to 32 ethylene oxide or propylene oxide units respectively, alkyl phenoxy polyoxyethylene containing 2 to 32 ethylene oxide units, alkyl phenoxy polyoxyethylene containing ethylene oxide units and 1 to 24 carbon atoms in the phenolic alkyl chain, and polyhydroxy compounds, including but not limited to, ethylene glycol, glycerol, or sorbitol.

X is selected from the group consiting of Group IA metals, Group IIA metals, transition metals, hydrogen, and an organic ion. The positively charge ion is not necessary for microbiocidal activity.

The microbiocidal additive of the present invention can be added to a wide variety of materials in accordance with the present invention to impart microbiocidal activity to those materials.

For example, the microbiocidal additive of the present invention can be added to aqueous solutions of detergents in accordance with the present invention to provide microbiocidal cleansing agents. In addition, the present invention can be added to water or other solvents to provide an effective disinfectant.

Additionally, the microbiocidal additive of the present invention can be added to both permanent and non-permanent coating materials in accordance with the present invention. When the coating material is applied to a surface, the microbiocidal additive that has been added to the coating material will impart long lasting microbiocidal activity to the surface.

Furthermore, the microbiocidal additive of the present invention can also be incorporated into a wide variety of plastics in accordance with the present invention to impart microbiocidal activity to the objects made from the plastics. When incorporated into the plastic material, the microbiocidal additive of the present invention inhibits the growth of microorganisms over a long period of time and protects the plastic from degradation by harmful microorganisms. In addition, the microbiocidal additive utilized in accordance with the present invention does not change the desirable properties of the plastic material.

The microbiocidal additive of the present invention can be applied topically to both natural and synthetic fibers in accordance with the present invention. The present invention can also be incorporated directly into synthetic fibers to impart microbiocidal activity to the fibers or to fabrics made from the fibers. In addition, the microbiocidal additive of the present invention can be applied directly to a fabric.

The microbiocidal additive of the present invention can also be added to coatings that are designed to coat surfaces that remain for long periods of time in water such as boat bottoms. Alternatively, the microbiocidal additive of the present invention can be incorporated into a material that is designed to remain in water for long periods of time. A material that is treated with the microbiocidal additive of the present invention will inhibit the growth of algae on the surface of the treated material.

As a final illustration, the above described microbiocidal additive of the present invention can be applied to materials as a preservative. For example, the additive can be applied to wood and wood products to inhibit the deterioration of the product due to microbiocidal growth. It has been determined that the microbiocidal additive of the present invention is effective in inhibiting infestation of insects, such as termites, in wood and is therefore a good preservative against insect infestation when applied to wood and wood products.

The microbiocidal additive utilized in practicing the present invention can also be mixed with liquids such as inks, fuels, and lubricating oils to inhibit the growth of microorganisms. The microbiocidal additive of the present invention is capable of killing the causitive organism of Legionaires' disease, *Legionella pneumophilia*. Thus, the present invention embraces addition of the identified compound to cooling tower water to control the growth of this pathological organism.

Accordingly, it is an object of the present ivention to provide for use of microbiocidally effective phosphate derivatives in and on a variety of products.

Another object of the present invention is to provide for the use of microbiocidally effective phosphate derivatives which can be added to an aqueous detergent to impart microbiocidal activity to the detergent.

Yet another object of the present invention is to provide for the addition of microbiocidally effective phosphate derivatives to water or other solvents to provide effective disinfectants.

Another object of the present invention is to provide for addition of microbiocidally effective phosphate derivatives to permanent and non-permanent coatings.

Another object of the present invention is to provide for incorporation of microbiocidally effective phosphate derivatives into plastics to provide a self-sanitizing plastic product with microbiocidal activity against a wide variety of organisms including bacteria, fungi, molds, algae and viruses.

Yet another object of the present invention is to provide for incorporation of microbiocidally effective phosphate derivatives into synthetic fibers or fabrics to provide a self-sanitizing fiber or fabric product with microbiocidal activity against a wide variety of organisms.

Another object of the present invention is to provide for incorporation of microbiocidally effective phosphate derivatives in objects and liquids to preserve the objects or liquids against degradation by microorganisms.

Another object of the present invention is to provide for incorporation into products or application onto products of microbiocidally effective phosphate derivatives to preserve the products from degradation by microorganisms.

Another object of the present invention is to provide a product that is effective in retarding or killing insects.

Another object of the present invention is to provide for the incorporation of microbiocidally effective phosphate derivatives into synthetic fibers or fabrics to provide a self-sanitizing fiber or fabric product with microbiocidal activity against a wide variety of organisms.

Another object of the present invention is to provide for the application of microbiocidally effective phosphate derivatives to the surface of both synthetic and natural fibers and fabrics to provide a self-sanitizing fiber or fabric product with microbiocidal activity against a wide variety of microorganisms.

Another object of the present invention is to provide phosphate derivatives which can be incorporated into conventional plastics which can then be molded or otherwise constructed to provide a plastic product with insecticidal activity.

Another object of the present invention is to provide an effective insecticidal phosphate derivatives which can be mixed with an aqueous detergent solution and used to wash an animal or object to kill or repel insects or related organisms.

Another object of the present invention is to provide a microbiocidal phosphate derivative These and other objects, features and advantages of the present invention will become apparent after a review of the following detailed description of the disclosed embodiment and the appended claims.

DETAILED DESCRIPTION OF THE PREFERRED EMBODIMENT

The present invention relates to microbiocidal and insecticidal compositions comprising certain derivatives of phosphates. When used in accordance with the present invention, the phosphate derivatives are capable of killing or inhibiting the growth of a wide variety of microorganisms including fungi, yeasts, viruses, algae and bacteria.

The phosphate derivative utilized in accordance with the present invention inhibits the growth of the following representative Gram-negative and Gram-positive bacteria: *Sarcina lutea*, Staphylococcus species, *Pseudomonas aeruginosa, Pseudomonas cepacia, Escherichia coli, Escherichia communior, Bacillus subtilis*, Klebsiella species, Salmonella species, *Legionella pneumophilia, Enterobacter aerogenes* and Streptococcus species. The phosphate derivative also inhibits the growth of the following representative fungi and yeasts: *Candida albicans, Trichophyton metagrophytes, Trichophyton rubrum, Trichophyton interdigitale* and *Aspergillus niger*. In addition, the phosphate derivative also inactivates *Herpes simplex* virus. The foregoing microorganisms are representative of those organisms that are responsible for infections in hospitals and other health care facilities.

The microbiocidal additive of the present invention can be added to water or other solvents to provide a disinfectant or can be added to a conventional detergent to provide a microbiocidal cleansing agent. The detergents that can be used in the present invention include, but are not limited to, linear alkyl sulfonates and alkyl benzene sulfonates. These detergents also include, but are not limited to, metal salts of long chain fatty acids.

Such a microbiocidal cleansing agent is effective in killing or significantly inhibiting the growth of a wide spectrum of both procaryotic and eucaryotic microorganisms which may reside on surfaces to be cleaned or treated with the microbiocidal detergent. Thus, in accordance with the present invention, it has been determined that certain phosphate derivatives impart fungicidal, algaecidal, viricidal and bactericidal properties to a conventional detergent.

The microbiocidal additives of the present invention can be mixed in water at various concentrations and be used as a disinfecting agent to kill or inhibit microorganisms that may reside on that surface. For example, a solution of the additive of the present invention containing from approximately 500 to 1000 parts per million (PPM) of the phosphate derivative makes an excellent disinfectant for light duty such as mopping and cleaning of hard surfaces such as vinyl walls, floors, counters and table tops.

For more demanding microbiocidal activity such as that required for a surgical scrub, the phosphate derivative can be mixed in with a conventional detergent at a concentration of between approximately 15% and 70% by weight.

The microbiocidal cleansing agent prepared by the addition of the microbiocidal additive of the present invention to a conventional cleansing agent has the capacity to kill or inhibit the growth of many types of bacteria, fungi, viruses, yeasts and other destructive or disease-producing microorganisms which might be on a surface. Such a microbiocidal cleansing agent is particularly effective against both Gram-positive bacteria, such as *Staphylococcus aureus*, and Gram-negative bacteria, such as *Pseudomonas aeruginosa*.

The microbiocidal additive of the present invention can also be added to a wide variety of permanent and non-permanent coating materials. These coatings include paints of various kinds, waxes, and plastic coatings. When the coating material is applied to a surface, the microbiocidal additive in the coating material will impart microbiocidal activity to the surface. The coating materials that can be used with the microbiocidal additive of the present invention include, but are not limited to, coatings formed from materials including the acrylate and methacrylate polymers and copolymers; the vinyl polymers including polyvinyl chloride, polyvinyl acetate, polyvinyl butyral, polyvinyl chloride-acetate, vinyl chloride-vinylidine chloride copolymers; the polyethylene polymers including polyethylene, polyhalogenated ethylenes, polystyrene and the styrenated alkyds. Further coating materials include thermosetting as well as other thermoplastic materials. Illustrative of such materials are the alkyd resins including the modified alkyds and the terpenic and maleic alkyds, the amino resins including urea-formaldehyde and melamine-formaldehyde; the protein plastics including casein, zein, keratin, peanut and soy bean plastics; the cellulosics including cellulose acetate, cellulose nitrate, cellulose acetate butyrate, regenerated cellulose, lignocellulose, ethyl cellulose, hydroxyethyl cellulose and carboxymethyl cellulose; the epoxy resins; the ethylene and fluoroethylene polymers; the furan resins; the polyamides; the phenolics including phenol-formaldehyde phenol-furfural and resorcinol-formaldehyde, the polyester resins including the saturated polyesters, the unsaturated polyesters and the polyfunctional unsaturated esters and the silicones.

The microbiocidal additive of the present invention can be mixed in accordance with the present invention with paint or other coatings and applied to underwater surfaces to inhibit the growth of marine organisms, such as algae, on such coated surfaces. For example, the microbiocidal additive of the present invention can be incorporated into paint and painted on a boat bottom. The treated coating will inhibit the growth of algae and other marine organisms on the bottom of the boat.

In addition, the microbiocidal additive can be incorporated into a material that is to be immersed in water for long periods of time to inhibit the growth of algae on the material. An example of such a use for the microbiocidal additive of the present invention is incorporating the microbiocidal additive of the present invention into fiberglass that is to be used to mold a boat bottom.

The microbiocidal additive of the present invention can be added to a coating material at a concentration of between approximately 0.01 to 10% by weight. The preferred concentration of phosphate derivative in the coating material is between about 0.1% and 6% by weight with an especially preferred concentration of between approximately 0.5% and 4% by weight.

The microbiocidal additive of the present invention can be incorporated into plastics to impart microbiocidal activity to the plastic products. Plastics treated with the present invention can be used to make a wide variety of products such as furniture, medical items, eating utensils and the like. There are many advantages to constructing products from plastic materials including lower cost and the possibility of molding the items in a variety of different shapes. Examples of the type of products contemplated include, but are not limited to, mattress covers, crib covers, bassinet covers, draw sheets, cubicle curtains, male and female urinals, toilet seats, bed pans, bed pan liners, wash basins, laminated sheets of melamine and phenolic plastics such as Formica TM, Micarta TM, and other similar decorative surfacing materials, carafes, tooth brushes, hair brushes, combs, soap holders, denture cups, rolls of utility sheeting, catheters, drainage bags, colostomy pouches, ileostomy pouches, intravenous solution bags, irrigation solution bags, blood bags, tubing, administration sets, donor sets, fountain syringes, enema bags, contact lens holders, examination equipment covers for all classes of trade including a medical doctor, veterinarian, dentists, optometrist, ophthalmologist, and optician, moisture barrier for the building trade to eliminate mold and mildew, table tops, food handling trays, wall paneling, hard floor covering, epoxy tiles, epoxy grout, ceramic tile grout, carpet base, shower curtains, bath mats, and telephone caps for mouth piece and reception unit. The product in some instances may be molded using standard plastic molding techniques. In other instances the product may be assembled from cut or molded parts into a finished product.

The phosphate derivative is present in the plastic material at a concentration of between approximately 0.1 and 10% by weight. A preferred range of phosphate derivative in the plastic material is between approximately 1% and 6% by weight.

The microbiocidal additive of the present invention can be applied topically to both natural and synthetic fibers or can be incorporated directly into synthetic fibers during the manufacturing process. The fibers that can be used with the microbiocidal additive of the present invention include but are not limited to fibers made of wool; cotton; polyolefin fiber including polypropylene, polybutenes, polyisoprene and their copolymers; polyester fiber including polyethylene terephthalate; polyaramid fiber; cellulose acetate fiber; rayon fiber; nylon fiber; polystyrene fiber; vinyl phenolic fiber; vinyl acetate fiber; vinyl chloride fiber; acrylic fiber; acrylonitrile fiber; and polyurethane fiber.

Fabrics can also be treated with the microbiocidal additive of the present invention. These fabrics include, but are not limited to, woven fabrics made from all of the aforementioned fibers or non-woven fabrics. The non-woven fabrics can be made, for instance, by entangling fibers in a needling process, by using a thermoplastic or adhesive backing or binder, or by fusing fibers together with heat.

The phosphate derivative can be applied to the fiber or fabric by mixing the phosphate derivative with a liquid such as water or other solvent or dispersant and then dipping, spraying or washing the fiber or fabric in the phosphate derivative mixture. The concentration of phosphate derivative in the water or other solvent or dispersant is between 0.01% and 30% by weight. The preferred concentration of phosphate derivative in dispersant or solvent is between 0.1% and 10% by weight. The most preferred concentration of phosphate derivative in dispersant or solvent is between 0.5% and 6% by weight. Suitable solvents that can be used to apply the phosphate derivative include, but are not limited to, benzene, toluene, xylene, and hexane. After applying the mixture, the fiber or fabric will be coated with the phosphate derivative. Therefore, when microorganisms comes into contact with the fiber or fabric, the phosphate derivative will kill or inhibit the growth of the microorganism.

The additive of the present invention can also be homogeneously distributed in a solvated fiber dope or a fiber melt before the fiber is spun at a concentration of between approximately 0.01% and 10% by weight. A preferred concentration of the phosphate derivative in fiber or fabric is between 0.1% and 6% by weight.

In accordance with the present invention, the phosphate derivative can be incorporated directly into natural or synthetic rubber, including latex rubber, polyvinyl acetate or polyvinyl chloride backings or binders that are applied to a fabric. It has been found that, when properly incorporated in accordance with the present invention, a portion of the microbiocidal additive of the present invention will slowly migrate from the fabric backing or binder onto the fibers of the fabric thereby imparting microbiocidal activity to the fabric.

Examples of the type of fiber or fabric products contemplated include, but are not limited to, surgical gauze, padding on wound dressings, mattress covers, crib covers, bassinet covers, sailboat sails, tents, draw sheets, cubicle curtains, tooth brushes, hair brushes, fabric wall covering, fabric base, fabric shower curtains, bath mats, athletic clothing such as underclothes, shirts, socks, shorts, pants, shoes and the like, and hospital clothing such as examination robes, physicians coats and nurses uniforms.

The microbiocidal additive of the present invention can be used as a preservative to prevent degradation of a product due to growth of microorganisms. For example, the phosphate derivative can be mixed with water or oil and sprayed on wood to preserve the wood against breakdown due to microorganisms. Small amounts of the derivative can be added to inks to prevent the growth of microorganisms which will clog ink jets. The derivative can be added to cutting oils to prolong the useful life of the oil. The additive is also useful in inhibiting growth of microorganisms in fuel and thereby decreasing the likelihood of clogged fuel jets.

In accordance with the present invention, the phosphate derivative can be added to the water in cooling towers or can be included in a coating that is used to coat the surfaces in cooling towers to kill or inhibit the growth of the pathogen that causes Legionaire's disease, *Legionella pneumophilia*.

The microbiocidal additive of the present invention can be used to coat air and other filter material and media thereby killing or reducing the growth of microorganisms in filters. The filter material can be particulate or can be fibrous in composition. When fluids pass through the filter and microorganisms are deposited upon the filter material or exposed to the filter material, the microbiocidal additive of the present invention will inhibit or kill the organism.

The phosphate additives can also be added in accordance with the present invention to various grouts, cements and concretes to impart microbiocidal activity to the material. For example, between about 0.01 and 10% of the microbiocidal compound of the present invention can be added to tile grout before application to a surface. The preferred concentration of the microbiocidal additive in grout, cement or concrete is between 0.1% and 6%. The present invention will prevent unsightly mold or mildew from growing in or on the grout, concrete, or cement material.

The microbiocidal phosphate additive has also been found to be an effective insecticidal agent and an insect repelling agent. When insects such as flies or fleas come into contact with a product treated with the microbiocidal additive of the present invention, the insects are killed or repelled. The insecticidal alkyl phosphate derivative, when used in accordance with the present invention, can be utilized as an aqueous mixture or can be incorporated into a number of materials such as plastics and the like.

When the phosphate derivative is mixed with water, it can be applied directly to a surface to impart insecticidal and insect repellant qualities to the surface. In addition, the insecticidal alkyl phosphate derivative of the present invention can be mixed with an aqueous detergent and used to wash objects or animals. For example, an aqueous detergent with the alkyl phosphate derivative makes an excellent soap for washing dogs and cats. The treated detergent kills any fleas that may be on the dog or cat and will repel any new fleas for a long period of time. The phosphate derivative of the present invention is not toxic to the dog or cat.

The phosphate derivative has also been found to be an effective deodorant.

Although not wanting to be bound by the following description of the mechanism of the microbiocidal additive of the present invention, it is believed that at least one free hydroxyl group on the phosphate group is necessary for Gram negative microbiocidal activity. Thus, if all of the hydroxyl groups are replaced with alkyl or other organic groups, the phosphate derivative will no longer exhibit microbiocidal activity. It is believed that, in general, the more hydroxyl groups that are free, the greater the microbiocidal activity that will be exhibited by the phosphate derivative.

Thus the microbiocidal additive of the present invention can be described as an alkyl phosphate ester having at least one free hydroxyl group. A "free hydroxyl group" is defined herein as "—OH".

The microbiocidal additive of the present invention can be more specifically defined as a phosphate ester with at least one free hydroxyl group with the following general formula:

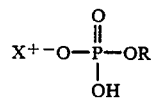

wherein:
- R may be alkyl, aryl, aralkyl and alkaryl groups including, but not limited to, straight chain, branched chain or cyclic alkyl groups having from 1 to 24 carbon atoms, polyoxyethylene or polyoxypropylene having from 2 to 32 ethylene oxide or propylene oxide units respectively, alkyl phenoxy polyoxyethylene containing 2 to 32 ethylene oxide units, alkyl phenoxy polyoxyethylene containing ethylene oxide units and 1 to 24 carbon atoms in the phenolic alkyl chain, and polyhydroxy compounds, including but not limited to, ethylene glycol, glycerol, or sorbitol
- R may also be hydrogen, but only if X is a quaternary amine.
- X is selected from the group consisting of Group IA metals, Group IIA metals, transition metals, hydrogen, and an organic ion. The positively charged ion is not necessary for microbiocidal activity.

A preferred structure of the phosphate derivative comprises the following formula:

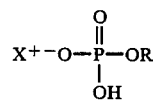

wherein:
- R=an alkyl group of from 6 to 18 carbon atoms.
- X is selected from the group consisting of Group IA metals, Group IIA metals, transition metals, hydrogen, and an organic ion. The microbiocidal additive defined by this formula is water insoluble or only slightly soluble in water and is especially useful for addition to non-aqueous products such as plastics, fibers and non-aqueous coatings. An aqueous suspension of the phosphates with the alkyl group of greater than 6 carbon atoms in the R position can be prepared by adding a surfactant such as Tween 80 (Sigma Chemical Company, St. Louis, MO) or other suitable nonionic surfactant.

An especially preferred structure of the microbiocidal additive of the present invention comprises a phosphate with the following formula:

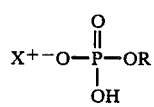

wherein:
- R=an alkyl group of from 1 to 5 carbon atoms.
- X is selected from the group consisting of Groupd IA metals, Group IIA metals, transition metals, hydrogen, and an organic ion.

The microbiocidal additive defined by this formula is water soluble and is especially useful as an additive for a disinfectant or for a detergent.

An additional preferred structure of the microbiocidal additive of the present invention has the following formula:

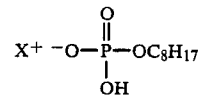

wherein:
- X is selected from the group consisting of Group IA metals, Groups IIA metals, transition metals, hydrogen, and an organic ion.

Another especially preferred embodiment of the present invention has the following formula:

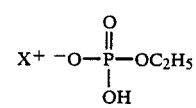

wherein:
- X is selected from the group consisting of Group IA metals, Group IIA metals, transition metals, hydrogen, and an organic ion.

This embodiment of the microbiocidal additive of the present invention is soluble in water.

When the additive utilized in accordance with the present invention is incorporated into a non-aqueous material such as a plastic or fiber, the microbiocidal activity of the product can be improved by substituting for "X" a large organic ion such as a quaternary amine. An example of such a compound is a tertiary amine with the following general formula:

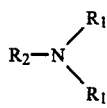

wherein:
$R_1$ = an alkyl group of from 1 to 18 carbon atoms or a hydroxy alkyl group of from 1 to 18 carbon atoms. The $R_1$ groups are not necessarily identical.
$R_2$ = an alkyl group of from 8 to 18 carbon atoms.

Another especially preferred embodiment of the present invention is an alkyl phosphate derivative with the following formula:

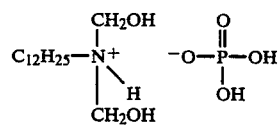

This especially preferred embodiment can be prepared by neutralizing phosphoric acid with between 1 to 2 moles of the tertiary amine. If more tertiary amine is used to neutralize the phosphoric acid, the free hydroxyls on the phosphate group will be eliminated and it is believed that the Gram negative microbiocidal activity of the compound will be diminished.

The type of component to be used as the "X" substituent will depend largely upon the compatibility of the base material for the "X" substituent.

The microbiocidal additive of the present invention may be prepared as follows: One mole of phosphorous pentoxide is reacted with between approximately 1 to 3 moles of an alcohol. The alcohol can be an alkyl or an aryl compound. The alkyl alcohol can be straight chained, branched chain or cyclic. The alcohol should be heated to a temperature of between approximately 60° and 120° C. depending upon the boiling point of the alcohol used.

The phosphorous pentoxide is slowly added to the alcohol while the mixture is vigorously agitated. The reaction is complete two to four hours after the addition of phosphorous pentoxide is completed.

The product formed in this reaction is a mixture of mono-ester phosphate and di-ester phosphate. The reaction equation is as follows:

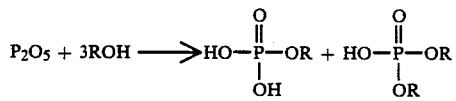

where R is the alkyl or aryl group depending upon the substituent used. It is to be understood that the mono-ester reaction product is the most microbiocidally active compound. It is believed that this is because the mono-ester has a free hydroxyl group. The di-ester reaction product is only slightly microbiocidally active.

The phosphate derivative is an effective microbiocidal compound and is capable of killing or inhibiting a wide variety of microorganisms including bacteria, yeasts, fungi, algae, molds and viruses.

The microbiocidal additive of the present invention can be modified to give the phosphate derivative physical properties which are particularly advantageous to the medium in which the phosphate derivative is to be used. For example, if it is desired to impart microbiocidal activity to a plastic material, it would be advantageous to have the phosphate derivative diffuse from the body of the plastic to the surface of the plastic where most of the microorganisms reside. To obtain a phosphate derivative that is capable of diffusing through a non-aqueous material, such as a fiber or plastic, to the surface of the material, the phosphate can be partially neutralized with a tertiary amine as shown in the following reaction equation:

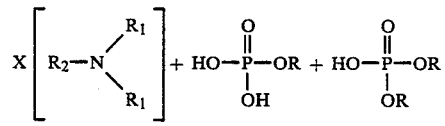

The preferable range for X is between approximately 1 and 1.5 moles with the especially preferable range of 1.3 moles.

This reaction results in a mixture of the following mono-alkyl phosphate amine product:

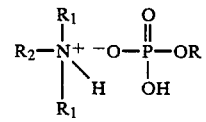

and the following di-alkyl phosphate amine product:

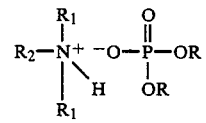

and the following monoalkyl phosphate:

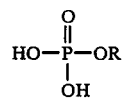

wherein:
R = a straight chain or a branched chain alkyl group of from 1 to 18 carbon atoms;
$R_1$ = an alkyl group of from 1 to 18 carbon atoms or a hydroxy alkyl group of from 1 to 18 carbon atoms.
$R_2$ = a straight chain or a branched chain alkyl group of from 8 to 18 carbon atoms.

Consistent with the proposed theory that the microbiocidal phosphate derivative requires at least one free hydroxyl, the di-alkyl phosphate amine has little microbiocidal activity. The mono-alkyl phosphate and the mono-alkyl phosphate amine both have microbiocidal activity.

To obtain a diffusable microbiocidal additive, the above reaction is carried out in the following manner: Between approximately 0.5 and 1.5 moles of the tertiary amine per mole each of the mixed phosphodiesters from the first reaction is slowly added to the mixture. This reaction is carried out at a temperature of between approximately 80° C. and 120° C. depending on the phosphate used. The most preferred tertiary amine is bis(hydroxyethyl) cocoamine. The preferred phosphate derivative that is capable of diffusing in a plastic material has the following formula:

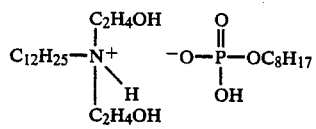

Although a tertiary amine with a long chain alkyl group is used in this embodiment to promote diffusion of the phosphate derivative of the present invention, it is to be understood that other tertiary amines could be used to promote diffusion. In addition, it should be noted that when 1 to 1.5 moles of tertiary amine are used to partially neutralize the alkyl phosphates, some alkyl phosphate monoester will be present in the solution.

The microbiocidal activity of the phosphate derivative of the present invention is evaluated as follows. Petri dishes are prepared using appropriate nutrient agar as a food source for the microorganism to be tested. The microorganism is seeded into the agar as is well known to one of ordinary skill in the art. A hole 6 mm in diameter and 5 mm deep is cut into the agar. 0.05 ml. of each of the indicated test compounds is placed in the hole and the inoculated petri dish is incubated for 24 hours at 37° C. After the 24 hour incubation period, the relative susceptibility of the test organisms to the phosphate derivative of the present invention is demonstrated by a clear zone of growth inhibition around the test solution. This zone of inhibition is the result of two processes: (1) the diffusion of the compound and (2) growth of the bacteria. As the phosphate derivative diffuses through the agar medium from the hole, its concentration progressively diminishes to a point where it is no longer inhibitory for the test organism. The area of the suppressed microbial growth, the zone of inhibition, is determined by the concentration of the phosphate derivative present in the area. Therefore, within the limitations of the test, the area of the inhibition zone is proportional to the relative susceptibility of the microorganisms to the phosphate derivative of the present invention.

After the 24 hour incubation period, each plate is examined and the diameters of the complete inhibition zones are noted and measured using either reflected light and a measuring device such as sliding calipers, a ruler, or a template prepared for this purpose and held on the bottom of the plate. The end point, measured to the nearest millimeter, is the point at which no visible growth that can be detected with the unaided eye minus the diameter of the test drop or sample. The area of the zone of inhibition is then calculated.

The following examples will serve to further illustrate the present invention without, at the same time, however, constituting any limitation thereof.

EXAMPLE I

The mono-ethyl alkyl phosphate derivative is prepared as follows: One mole of phosphorous pentoxide is reacted with three moles of ethanol at a temperature of 60° C. The phosphorous pentoxide is slowly added to the ethanol while the mixture is vigorously agitated. At the reaction temperature of 60° C. the reaction is complete in about two hours. The progress of the reaction is determined by titrating the acid that is produced with a solution of potassium hydroxide. The reaction products include approximately equimolar quantities of the mono-ethyl alkyl phosphate and the di-ethyl alkyl phosphate. The mono-ethyl alkyl phosphate is the more microbiocidally active species.

EXAMPLE II

The mono-(2-ethylhexyl) phosphate derivative is prepared as follows. One mole of phosphorous pentoxide is reacted with three moles of 2-ethylhexanol at a temperature of 100° C. The phosphorous pentoxide is slowly added to the alcohol while the mixture is vigorously agitated. At the reaction temperature of 100° C. the reaction is complete in about two hours. The progress of the reaction is determined by titrating the acid that is produced with a solution of potassium hydroxide. The reaction products include approximately equimolar quantities of the mono-(2-ethylhexyl) alkyl phosphate and the di(2-ethylhexyl) alkyl phosphate. The mono-(2-ethylhexyl) alkyl phosphate is the more microbiocidally active species.

EXAMPLE III

Since the preferred method of preparing the phosphate of Examples I and II results in two reaction products, the monoalkyl phosphate and the di-alkyl phosphate, the relative microbiocidal activity of each of the products is evaluated.

Three samples are tested:
1. 91% mono-(2-ethylhexyl) phosphate, 9% di-(2-ethylhexyl)phosphate
2. 55% mono-(2-ethylhexyl)phosphate and 45% di-(2-ethylhexyl)phosphate
3. 95% di-(2-ethylhexyl) phosphate, 5% mono-(2-ethylhexyl)phosphate.

Petri dishes are prepared using trypticase soy nutrient agar (Baltimore Biological Laboratory, Cockeysville, MD). The microorganisms used in this test are the Gram-positive *Staphylococcus aureus* and the Gram-negative *Pseudomonas aeruginosa*. Each microorganism is seeded into the agar as is well known to one of ordinary skill in the art. A hole 6 mm in diameter and 5 mm deep is cut into the agar. 0.05 ml. of each of the indicated test compounds is placed in the hole, and the inoculated petri dish is incubated for 24 hours at 37° C. After the 24 hour incubation period, the relative susceptibility of the test organisms to the phosphate derivative of the present invention is demonstrated by a clear zone of growth inhibition around the test solution.

After the 24 hour incubation period, each plate is examined and the diameters of the complete inhibition zones are noted and measured as described above. Each test is performed at least 6 times. The areas shown in Table A are the average of the 6 separate tests.

TABLE A

| Organism | Zone of Inhibition in mm$^2$ | | |
|---|---|---|---|
| | 91% Mono-ester 9% Di-ester | 55% Mono-ester 45% Di-ester Mixture | 95% Di-ester 5% Mono-ester |
| S. aureus | 352 | 240 | 148 |
| P. aeruginosa | 319 | 148 | 28 |

The results of Table A indicate that the mono-alkyl phosphate is the compound which has the significant amount of the microbiocidal activity.

EXAMPLE IV

To produce a microbiocidal alkyl phosphate amine that can be used with a detergent to make a microbiocidal detergent approximately one mole each of the reaction products of Example II are partially neutralized with 1.3 moles of bis(hydroxyethyl) cocoamine. 1.3 moles of bis(hydroxyethyl) cocoamine is slowly added to the reaction products of Example II until the pH is between approximately 3.2 and 3.8 in 75% ethanol. This reaction is carried out at a temperature of 100° C. The reaction mixture is vigorously agitated during the reaction.

An aqueous mixture of the microbiocidal alkyl phosphate is prepared by mixing the alkyl phosphate derivative from Example II with an aqueous detergent solution. The concentration of alkyl phosphate derivative is 0.05%. The microbiocidal detergent is heated to 85° C. Cotton fabric is then introduced and remains in the heated solution for 15 minutes. The fabric is then rinsed in water at 40° C., removed, and dried.

Square samples of the treated fabric of approximately 400 mm$^2$ are cut and placed on agar plates which have previously been inoculated with *Staphylococcus aureus* and *Pseudomonas aeruginosa;;* the plates are then incubated at 35° C. for 24 hours.

After the 24 hour incubation, neither *Staphylococcus aureus* nor *Pseudomonas aeruginosa* are found to be present in or on the squares. Microscopic examination shows a zone of inhibition around the individual threads.

EXAMPLE V

To produce a microbiocidal alkyl phosphate derivative that can be used with a detergent to make a microbiocidal detergent, the reaction product of Example II is neutralized with bis(hydroxyethyl) cocoamine. 1.3 moles of bis(hydroxyethyl) cocoamine per mole of the reaction product from Example I is slowly added to the reaction product from Example II until the pH is between approximately 3.2 and 3.8 in a 75% ethanol solution.

EXAMPLE VI

To produce a microbiocidal alkyl phosphate derivative that is capable of migrating from the interior of a synthetic fiber, fabric or plastic to the surface, the reaction product of Example II is partially neutralized with bis(hydroxyethyl) cocoamine. 1.3 moles of bis(hydroxyethyl) cocoamine per mole of the reaction product from Example II is slowly added to the reaction product from Example II until the pH is between approximately 3.2 and 3.8 in a 75% ethanol solution. This reaction is carried out at a temperature of 100° C. The reaction mixture is vigorously agitated during the reaction.

The resulting product is only slightly soluble in water and is suitable for incorporation into synthetic fibers and plastics as they are being formed or for topical application in an organic solvent such as ethyl alcohol, benzene or xylene.

EXAMPLE VII

The microbiocidal capability of an alkyl phosphate amine is demonstrated by the following example. Between 0.5 moles and 3.0 moles of bis(hydroxyethyl) cocoamine per mole of the reaction product from Example II is slowly added to the reaction product from Example II until the pH of the solution is between approximately 2.5 and 6 in a 75% ethanol solution. This reaction is carried out at a temperature of 100° C. The reaction mixture is vigorously agitated during the reaction. The resulting compounds are tested for microbiocidal activity.

Petri dishes are prepared using trypticase soy nutrient agar (Baltimore Biological Laboratory, Cockeysville, MD). The microorganisms used in this test are the Gram-positive *Staphylococcus aureus* and the Gram-negative *Pseudomonas aeruginosa*. The microorganisms are seeded into nutrient agar as is well known to one of ordinary skill in the art. A hole 6 mm in diameter and 5 mm deep is cut into the agar. 0.05 ml. of each of the indicated test compounds is placed in the hole and the inoculated pertri dish is incubated for 24 hours at 37° C. After the 24 hour incubation period, the relative susceptibility of the test organisms to the phosphate derivative of the present invention is demonstrated by a clear zone of growth inhibition around the test solution.

After the 24 hour incubation period, each plate is examined and the diameters of the complete inhibition zones are examined and the diameters of the complete inhibition zones are noted and measured.

The results are summarized in Table C.

TABLE C

| | Molar Ratio of reactants | S. aureus | P. aeruginosa |
|---|---|---|---|
| | | Area of Inhibition measured in mm$^2$ | |
| A. | Product from Example II | 3848 | 706 |
| B. | 0.5 moles cocoamine$^a$ | 1520 | 614 |
| C. | 1.0 moles cocoamine$^a$ | 907 | 706 |
| D. | 1.3 moles cocoamine$^a$ | 452 | 1257 |
| E. | 1.5 moles cocoamine$^a$ | 452 | 38 |
| F. | 2.0 moles cocoamine$^a$ | 452 | 13 |
| G. | 2.5 moles cocoamine$^a$ | 201 | 13 |
| H. | 3.0 moles cocoamine$^a$ | 153 | 0 |
| I. | Cocoamine only | 153 | 0 |

$^a$Moles of cocoamine reacted with one mole of the product from Example II.

As can be seen in Table C, sample A, which is the reaction product from Example II, has excellent microbiocidal activity against both the Gram positive *Staphylococcus aureus* and the Gram negative *Pseudomonas aeruginosa*. The reaction product from Example II retains its microbiocidal activity against both these organisms even when reacted with up to 2 moles of the bishydroxyethyl cocoamine. When one mole each of the reaction product from Example II is reacted with more than 2 moles of the cocoamine, the microbiocidal activity is diminished. Although not wanting to be bound to the following mechanism, it is thought that the reduction is microbiocidal activity above 2 moles of the cocoamine is due to the neutralization of the free hydroxy group on the phosphate group. Three moles of cocoamine would theoretically neutralize all of the hydroxyl groups on the phosphate group and therefore eliminate the microbiocidal activity. The cocoamine itself has slight microbiocidal activity against the Gram positive *Staphylococcus aureus*. Thus, by partially neutralizing the 2-ethylhexyl phosphate with the bishydroxyethyl cocoamine, the antimicrobial activity of the phosphate is retained, and the compound now has the capability of diffusing from the interior to the surface of a synthetic fiber or a plastic material.

EXAMPLE VIII

The amine phosphate derivative from Table C, Line D of Example VII is added to a tumble-mixing machine containing polyethylene pellets so that the final concentration of alkyl phosphate derivative is 2% by weight. The thermoplastic pellets are tumble mixed until the alkyl phosphate derivative of the present invention is thoroughly distributed. After the sanitizing additive is mixed with and coated on the pelletized plastic material, the mixture is charged to a hopper of a conventional melt extruder where the mixture is melted and the sanitizing additive is homogeneously distributed throughout the melted mass by the action of the extruder. The resultant molten mass of plastic material is passed through a conventional spinneret to generate thermoplastic fibers containing the alkyl phosphate derivative.

EXAMPLE IX

The phosphate derivative from Table C, Line D of Example VII is added to a tumble-mixing machine containing polyethylene terephthalate polyester pellets so that the final concentration of phosphate derivative is 2% by weight. The thermoplastic pellets are tumble mixed until the alkyl phosphate derivative of the present invention is thoroughly distributed. After sanitizing additive is mixed with and coated the pelletized plastic material, the mixture is charged to a hopper of a conventional melt extruder where the mixture is melted and the sanitizing additive is homogeneously distributed throughout the melted mass by the action of the extruder as is well known to one of ordinary skill of the art. The resultant molten mass of plastic material is passed through a conventional spinneret to generate polyester fibers containing the alkyl phosphate derivative.

EXAMPLE X

The alkyl phosphate amine derivative from Table C, Line D of Example VII is used to prepare a self-sanitizing plastic material in accordance with the present invention. 1.0 part of the compound prepared in Example VII is added to one hundred parts of polyethylene pellets. The pellets are coated with the oily additive by tumbling the mixture for twenty minutes. The pellets so treated are then fused in a test tube by immersing the test tube in an oil bath at 200° C. for twenty minutes. The test tube is then removed from the oil bath and allowed to cool to room temperature whereupon the molten mass solidifies. The cooled mass in then removed from the test tube and sawed into discs approximately 2 mm thick and 10 mm in diameter. No degradation or other unusual characteristics of the polyethylene discs is noted. The discs are placed in appropriately inoculated petri dishes containing nutrient agar. The agar is inoculated with various organisms and is allowed to incubate for 24 hours at 37° C. After the incubation period, the zone of inhibition around the discs is measured as previously described. The results are presented in Table D.

TABLE D

| Organism | Type of Organism | Area of Inhibition in $mm^2$ |
|---|---|---|
| Staphylococcus aureus | Gram-pos. bacteria | 314 |
| Pseudomonas aeruginosa | Gram-neg. bacteria | 50 |
| Escherichia coli | Gram-neg. bacteria | 113 |
| Klebsiella species | Gram-neg. bacteria | 201 |
| Candida albicans | Yeast | 314 |
| Salmonella choleraesuis | Gram-neg. bacteria | 153 |
| Aspergillus niger | Fungus | 314 |
| Tricophyton mentagrophyte | Fungus | 707 |

As can be seen in Table D, the test demonstrates significant bactericidal activity against both Gram negative and Gram positive organisms as well as against representative yeasts and fungi.

EXAMPLE XI

An epoxy resin using the alkyl phosphate derivative is formulated as follows:

| | |
|---|---|
| Epoxy resin | 88.2% by weight |
| TIO2 | 9.8% by weight |
| Alkyl phosphate | 2.0% by weight from Example VII Table C, Line D |

The epoxy resin used in this example is referred to as DGEPPA or diglycidyl ether of bisphenol-A (Dow Chemical Company, Midland, MI). Other epoxy resins that can be used with the present invention are epichlorohydrin/bisphenol-A, glycidated novolacs, epoxylated novolacs, and cycloaliphatic epoxy resins.

After thoroughly mixing the above ingredients, the resin system is allowed to react with a stoichiometric amount of hardener (cross linking reagent). Before the cross-linking reaction is completed, samples of he self-sanitizing epoxy are poured into 100×15 mm test tubes. Upon completion of the hardening reaction, the epoxy sample is a hard cylinder measuring 60 mm long and 15 mm in diameter and weighing approximately 28.89 grams. Samples are cut in the form of discs with a surface area of 176.63 $mm^2$. The cut samples are placed in petri dishes containing nutrient agar (Trypticase Soy Nutrient Agar, Baltimore Biological Laboratory, Cockeysville, MD) inoculated with a lawn of the indicated microorganisms. It is found, upon incubation of the dishes that the epoxy disc inhibits the growth of bacteria and fungi around the specimen and creates a zone of inhibition. The results of the test are summarized in Table E.

TABLE E

| Organism | Type of Organism | Area of Inhibition in $mm^2$ |
|---|---|---|
| Staphylococcus aureus | Gram-pos. bacteria | 314 |
| Pseudomonas aeruginosa | Gram-neg. bacteria | 28 |
| Escherichia coli | Gram-neg. bacteria | 380 |
| Klebsiella species | Gram-neg. bacteria | 380 |
| Candida albicans | Yeast | 153 |
| Salmonella choleraesuis | Gram-neg. bacteria | 452 |
| Aspergillus niger | Fungus | 28 |
| Tricophyton mentagrophyte | Fungus | 50 |
| Bacillus megaterium | Gram-pos. bacteria | 13 |

As shown in Table E, the alkyl phosphate derivative, when added to epoxy resins, is effective in killing a wide variety of species of microorganisms.

EXAMPLE XII

The insecticidal activity of the alkyl phosphate derivative is shown in this Example. The minimum dose to kill 100% of a population of crickets (*Acheta domesticus*) is first determined. A test chamber is prepared for testing each concentration of the alkyl phosphate amine derivative from Table C, Line D of Example VII. The test chambers are constructed as follows: Plastic petri dish bottoms are secured to a piece of plywood. Five crickets are placed in to each dish. A piece of wire window screen is placed over each dish. Each dish was sprayed with approximately 0.5 ml of a solution of the alkyl phosphate derivative from Example II. The alkyl phosphate amine was mixed with water. The concentrations of the alkyl phosphate amine that are tested are as follows: 0.08%, 0.12%, 0.16%, and 0.2%. The results of the test are summarized in Table F.

TABLE F

| Sample | Time of observation | Results |
|---|---|---|
| Control | 5 min. | all 5 insects alive |
| | 30 min | all 5 insects alive |
| | 24 hours | all 5 insects alive |
| 0.08% Alkyl Phosphate | 5 min | 2 alive, 3 dead |
| | 30 min | 2 alive, 3 dead |
| | 24 hours | 2 alive, 3 dead |
| 0.12% Alkyl Phosphate | 5 min | 4 alive, 1 dead |
| | 30 min | 4 alive, 1 dead |
| | 24 hours | 2 alive, 3 dead |
| 0.16% Alkyl Phosphate | 5 min | 2 alive, 3 dead |
| | 30 min | 2 alive, 3 dead |
| | 24 hours | 1 alive, 4 dead |
| 0.2% Alkyl Phosphate | 5 min | 1 alive (weak), 4 dead |
| | 30 min | 1 alive (weak), 4 dead |
| | 24 hours | all five dead |

The mechanism of insecticidal activity appears to be different than that of the microbiocidal activity. The phosphate derivative without the quaternary amine group has no insecticidal activity and the quaternary amine group by itself will not kill the insects tested.

EXAMPLE XIII

The insecticidal activity of the alkyl phosphate amine derivative from Table C, Line D of Example VII that was distributed in a polyethylene sheet is tested. A polyethylene film is prepared by adding 90.72 grams of the alkyl phosphate derivative prepared in Example II to 52.5 pounds of polyethylene resin pellets and tumbling the mixture until the alkyl phosphate derivative is homogeneously distributed in the pellet mixture. The treated polyethylene pellets are then extruded in a commercial extruder to form a polyethylene film that has a thickness of approximately 4 mils. A control film is extruded with polyethylene that does not contain any alkyl phosphate derivative.

Circular test samples of both the alkyl phosphate derivative treated polyethylene film and control polyethylene film are cut to fit the bottom of a 15×100 mm petri dish. The circular test samples containing the alkyl phosphate derivative are placed in the bottom of petri dishes and the circular test samples that do not contain alkyl phosphate derivative are placed in the bottom of separate petri dishes. Four insects are used to test the insecticidal activity of the alkyl phosphate derivative as follows: cockroaches, ticks, houseflies, and fleas. The insects are placed in individual petri dishes with either the treated polyethylene film or the control polyethylene film and observed. The time that the insect dies is noted for both alkyl phosphate treated polyethylene film and untreated polyethylene film. The results of the test are shown in Table G.

TABLE G

| Test Film | Roach | Tick | Fly | Flea |
|---|---|---|---|---|
| Phosphate Treated Film | 30 min | 8 hours | 8 hours | 30 min |
| Control Film | | Alive after 8 hours | | |

There is no noticeable impairment of the insects that were placed in the petri dishes with the untreated polyethylene film after 8 hours.

EXAMPLE XIV

In this example, the alkyl phosphate derivative from Table D, Line D of Example VII is used to prepare a self-sanitizing vinyl product in accordance with the present invention. A polyvinyl chloride (PVC) system using the microbiocidal additive of the present invention is formulated as follows:

| Test Sample | |
|---|---|
| 100 | Grams of polyvinyl chloride |
| 55 | Grams of dioctylphthalate (plasticizer) |
| 1.5 | Grams Stabilizer |
| 9.0 | Grams $TiO_2$ |
| 1.0 | Grams Color concentrate |
| 3.5 | Grams alkyl phosphate from Table D, Line D of Example VIII |
| Control | |
| 100 | Grams of polyvinyl chloride |
| 55 | Grams of dioctylphthalate (plasticizer) |
| 1.5 | Grams Stabilizer |
| 9.0 | Grams $TiO_2$ |
| 1.0 | Grams Color concentrate |

The above samples are then poured on glass plates to a thickness of approximately 0.25 cm and cured in an oven at a temperature of approximately 325° F. After the sample has polymerized, test specimens from each formulation are cut into circles approximately 2 cm across.

Two test organisms are seeded on two separate petri dishes of agar. One dish is seeded with *Staphylococcus aureus* at a concentration of greater than $10^3$ organisms per ml. The second dish is seeded with *Pseudomonas cepacia* at a concentration of greater than $10^3$ organisms per ml.

One plug each of the test vinyl sample with the alkyl phosphate amine derivative added and the control vinyl sample with no alkyl phosphate are placed onto the surface of the agar in each inoculated petri dish. The dishes are incubated in a humidified incubation chamber at a temperature of approximately 37° C. for 24 hours. At the end of the 24 hour incubation period, the dishes are removed from the incubator and the area of clear zone of inhibition around the test samples is measured. The clear zone of inhibition around the samples represents inhibition of growth of bacteria due to the diffusion of antimicrobial alkyl phosphate from the vinyl plug. The results of the test are shown in Table H.

TABLE H

| | Test Organism Zone of inhibition in $mm^2$. | |
|---|---|---|
| Sample | *Staphylococcus aureus* | *Pseudomonas cepacia* |
| Test vinyl | 50 | 50 |
| Control | 0 | 0 |

As can be seen in Table H, the test demonstrates significant bactericidal activity against both Gram negative and Gram positive organisms.

EXAMPLE XV

In this example, the alkyl amine phosphate derivative from Table C, Line D of Example VII is used to produce a microbiocidal fiber. The phosphate derivative from Table C, Line D, of Example VII is melt spun with four polymers at a concentration of 1–2% by weight. The polymers that are used in this example are polypropylene, polyethylene, nylon and polyester.

Polyethylene with and without the alkyl phosphate amine and the polyester with the additive gave poor spinning performance and did not produce a satisfactory package of spun yarn. The other fibers produced are drawn at about 3/1 draw ratio and tested for tensile properties. The properties appear adequate for normal apparel type textile fibers being in the range of 3–4 grams force per denier and 20 to 40% elongation at the brake point. The addition of the microbiocidal additive or the present invention causes a small to moderate decrease in both tenacity and breaking elongation, but still produces fibers with adequate tensile properties for textile applications.

Polypropylene is extruded with few if any problems. The extrusion temperature is set at approximately 200° C. for zone 1 and about 225° C. for the other three zones. A small amount of Carbowax (1500) is diluted in water to about 20% and is used as a spin finish. The spin finish is selected because it is not likely to affect the results of antibacterial testing and because the material will wash off in water. Drawing of the polypropylene is done cold at about 3/1 draw ratio on a four roll draw winding stand designed by Bouligny. At least five tensile tests are run on each sample. Denier is determined from the weight of a 90 cm sample (weight measured to the nearest 0.1 mg) on an analytical balance. The strain rate is 100% per minute on a five inch sample.

| Properties of Polyethylene Yarn | | |
| --- | --- | --- |
| Physical Properties | Polypropylene Control | Polypropylene with additive |
| denier(g/9000 M) | 179 | 174 |
| tenacity (g/denier) | 4.15 | 3.95 |
| breaking elongation (%) | 30.4 | 23.3 |

Nylon is successfully extruded at a temperature of 260° C. in zone 1 and 280° C. to 290° C. in the other zones. The spin finish is Carbowax in water. Samples are drawn at slightly less than 3/1 draw ratio with a top roll temperature of 50° C.

Polyester is spun under conditions similar to nylon. When the microbiocidal alkyl phosphate amine is added, the nylon became light brown and excessive dripping at the spinnerette is noted. The problem can be reduced by reducing the concentration of the microbiocidal alkyl phosphate amine in the feed chips and by optimizing the extrusion temperature.

| Properties of Nylon Yarn | | |
| --- | --- | --- |
| Physical Properties | Nylon Control | Nylon with additive |
| denier (g/9000 M) | 280 | 251 |
| tenacity (g/denier) | 3.33 | 2.98 |
| breaking elongation (%) | 42.4 | 27.3 |

A polyethylene sample is extruded under conditions similar to those used with polypropylene. The polyethylene is a linear low density, fiber-grade polyethylene. Polyethylene fibers are collected as both control (no microbiocidal alkyl phosphate amine present) and fiber with approximately 1.25% microbiocidal alkyl phosphate amine present.

EXAMPLE XVI

Each of the fibers that is prepared in Example XV are evaluated for microbiocidal activity by the following procedure:

Nutrient media is prepared and divided into three portions. One portion is seeded from a twenty-four hour culture of *Staphylococcus aureus*. This organism is representative of Gram positive bacteria. The second portion is seeded from a twenty-four hour culture of *Pseudomonas aeruginosa*. This bacteria is representative of the Gram negative bacteria. The third portion of the nutrient media is seeded from a twenty-four hour culture of *Corynebacterium diphtheriae*.

The appropriate seed agar is poured into 150×50 mm sterile petri dishes (separate dishes for each bacteria). The seeded agar is allowed to solidify. The test fibers, along with the control fibers containing no alkyl phosphate amine, are placed on the agar and incubated for 24 hours at 37° C. After the twenty four hours incubation, the fibers are examined using a 20 power stereomicroscope. Zones of inhibition are observed around each fiber containing the alkyl phosphate amine indicating that the fiber is microbiocidal. No inhibition of growth is noted on or around any of the control fibers.

EXAMPLE XVII

The algaecidal activity of the microbiocidal additive of the present invention was evaluated as follows:

Three samples of different polymers are suspended in a 20 gallon glass aquarium which is filled with pond water and seeded with a variety of fresh water algae. An air pump is attached to the glass tank to keep the oxygen concentration in the water at a constant value. No agitation of the water other than that caused by the air bubbles occurs. The polymer samples remain in the aquarium for 60 days. At the end of 60 days, the samples are removed and evaluated. Following evaluation, all samples are subjected to flowing water from a faucet at full pressure of forty pounds about 6 inches from the faucet opening for a period of 60 sixty seconds.

During the 60 day test period, observations are made daily and during the first 14–20 days the polymers varies in resistance to algae accumulation when compared to the controls. Controls begin accumulating algae within 48 hours. When the treated polymers are disturbed by the running water, the algae is easily washed off of the sample. When the control samples are exposed to the running water, the algae is not washed off the sample. Although some algae does grow on the treated polymers, it is found that the algae is not securely anchored to the treated polymer. The algae is very securely anchored to the control, untreated polymers.

While this invention has been described in detail with particular reference to preferred embodiments thereof, it will be understood that variations and modifications can be effected within the spirit and scope of the invention as described hereinbefore and as defined in the appended claims.

I claim:

1. A biocidal polymeric composition comprising:
   (a) a polymeric material selected from the group consisting of synthetic polymers, natural polymers, paints, waxes, and fibers, and
   (b) a biocidally effective amount of a phosphate ester having the general formula;

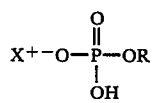

wherein R is selected from the group consisting of alkyl, aryl, aralkyl, and alkaryl groups, and X is $N(R_1)_2R_2$, wherein $R_1$ is a hydroxy alkyl group of from 1 to 18 carbon atoms, and $R_2$ is an alkyl group of from 8 to 18 carbon atoms.

2. The biocidal composition of claim 1 wherein R is an alkyl group of from 1 to 18 carbon atoms.

3. The biocidal polymeric composition of claim 1 or 2, wherein said polymeric material forms a coating.

4. The biocidal polymeric composition of claim 1 or 2, wherein said polymeric material forms a fiber.

5. The biocidal composition of claim 1 selected from the group consisting of:

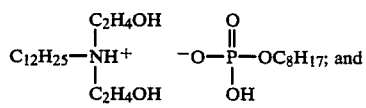

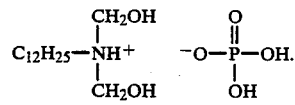

6. The biocidal composition of claim 1, wherein the phosphate ester is added in a range of 0.1 to 10% by weight.

7. The biocidal composition of claim 1, wherein the phosphate ester is applied topically to the polymer.

8. The biocidal composition of claim 1, wherein the phosphate ester is incorporated in the polymer.

9. A method for inhibiting the growth of microorganisms on or in a material selected from the group consisting of synthetic polymers, natural polymers, waxes, paints, and fibers, comprising adding a biocidally effective amount of a compound having the structure:

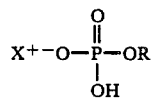

wherein R is selected from the group consisting of alkyl, aryl, aralkyl, and alkaryl groups, and X is selected from the group consisting of H, Group IA metals, Group IIA metals, transition metals, and $N(R_1)_2R_2$, wherein $R_1$ is an alkyl group of from one to eighteen carbon atoms or a hydroxy alkyl group of from 1 to 18 carbon atoms, and $R_2$ is an alkyl group of from 8 to 18 carbon atoms.

10. The method of claim 9, wherein $X^+$ is $N(R_1)_2R_2$.

11. The method of claim 9, wherein the compound is

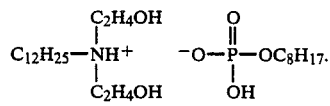

12. The method of claim 9, further comprising adding between 0.1 and 10% of the compound to the material.

13. An article of furniture constructed from the plastic material of claim 1.

14. An article of sports apparel constructed from the fabric of claim 1.

15. A fabric constructed from the polymeric composition of claim 1.

* * * * *